(12) United States Patent
Miyachi

(10) Patent No.: US 11,986,348 B2
(45) Date of Patent: May 21, 2024

(54) ULTRASOUND SYSTEM AND METHOD FOR CONTROLLING ULTRASOUND SYSTEM

(71) Applicant: FUJIFILM Corporation, Tokyo (JP)

(72) Inventor: Yukiya Miyachi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 87 days.

(21) Appl. No.: 17/062,671

(22) Filed: Oct. 5, 2020

(65) Prior Publication Data

US 2021/0015459 A1 Jan. 21, 2021

Related U.S. Application Data

(63) Continuation of application No. PCT/JP2019/015113, filed on Apr. 5, 2019.

(30) Foreign Application Priority Data

Apr. 25, 2018 (JP) .................................. 2018-083744

(51) Int. Cl.
*A61B 8/00* (2006.01)
*A61B 8/08* (2006.01)

(52) U.S. Cl.
CPC .......... *A61B 8/4472* (2013.01); *A61B 8/4494* (2013.01); *A61B 8/461* (2013.01); *A61B 8/5246* (2013.01)

(58) Field of Classification Search
CPC ....... A61B 8/4472; A61B 8/4494; A61B 8/00; A61B 8/461; A61B 8/5246; A61B 8/56; H04N 19/124; H04N 19/60
See application file for complete search history.

(56) References Cited

U.S. PATENT DOCUMENTS

2003/0181811 A1* 9/2003 Amemiya ............ A61B 8/4472
600/437
2008/0009737 A1* 1/2008 Takimoto ................. A61B 8/06
600/443

(Continued)

FOREIGN PATENT DOCUMENTS

CN 101569539 A 11/2009
DE 102005005386 B3 * 7/2006 ............. G01N 29/07

(Continued)

OTHER PUBLICATIONS

International Search Report issued in PCT/JP2019/015113 ; mailed Jun. 18, 2019.

(Continued)

*Primary Examiner* — Shahdeep Mohammed
*Assistant Examiner* — Fikirte (Fiki) T Ashine
(74) *Attorney, Agent, or Firm* — Studebaker & Brackett PC

(57) ABSTRACT

An ultrasound system 1 includes an ultrasound probe 2 and an image display device 3 that are wirelessly connected to each other. The ultrasound probe 2 includes a transducer array 11, a transmitting and receiving unit 14 that generates a sound ray signal by directing the transducer array 11 to transmit and receive ultrasonic waves, an image information data generation unit 20 that generates image information data from the sound ray signal, a compression unit 18 that compresses the image information data, and a compression ratio setting unit 23 that sets a compression ratio of the image information data. The image display device 3 includes a decompression unit 33, a display unit 36 that displays an ultrasound image based on the decoded image information data, and an inspection mode setting unit 39 that sets an inspection mode. The compression ratio setting unit 23 sets the compression ratio corresponding to the inspection mode and the compression unit 18 compresses the image information data at the set compression ratio.

13 Claims, 6 Drawing Sheets

(56) References Cited

U.S. PATENT DOCUMENTS

| | | | |
|---|---|---|---|
| 2012/0220877 A1* | 8/2012 | Takeshima | H04N 19/136 367/87 |
| 2012/0226164 A1* | 9/2012 | Tashiro | G01S 15/8927 600/461 |
| 2015/0297193 A1 | 10/2015 | Rothberg et al. | |
| 2016/0331353 A1 | 11/2016 | Ralston et al. | |
| 2017/0086798 A1 | 3/2017 | Bjaerum et al. | |
| 2019/0216436 A1* | 7/2019 | Miyazawa | A61B 8/54 |

FOREIGN PATENT DOCUMENTS

| | | | | |
|---|---|---|---|---|
| JP | H08-308836 A | | 11/1996 | |
| JP | 2002-017732 A | | 1/2002 | |
| JP | 2002017732 A | * | 1/2002 | |
| JP | 2006-296633 A | | 11/2006 | |
| JP | 2008-253378 A | | 10/2008 | |
| JP | 2015-211726 A | | 11/2015 | |
| WO | WO-2018066434 A1 | * | 4/2018 | ........... A61B 5/0095 |

OTHER PUBLICATIONS

Written Opinion issued in PCT/JP2019/015113; mailed Jun. 18, 2019.

The extended European search report issued by the European Patent Office on May 7, 2021, which corresponds to European Patent Application No. 19792612.4-1126 and is related to U.S. Appl. No. 17/062,671.

An Office Action mailed by China National Intellectual Property Administration on Aug. 5, 2023, which corresponds to Chinese Patent Application No. 201980027873.2 and is related to U.S. Appl. No. 17/062,671; with English language translation.

* cited by examiner

ULTRASOUND SYSTEM AND METHOD FOR CONTROLLING ULTRASOUND SYSTEM

CROSS-REFERENCE TO RELATED APPLICATIONS

This application is a Continuation of PCT International Application No. PCT/JP2019/015113 filed on Apr. 5, 2019, which claims priority under 35 U.S.C. § 119(a) to Japanese Patent Application No. 2018-083744 filed on Apr. 25, 2018. The above application is hereby expressly incorporated by reference, in its entirety, into the present application.

BACKGROUND OF THE INVENTION

1. Field of the Invention

The present invention relates to an ultrasound system and a method for controlling the ultrasound system, and more particularly, to an ultrasound system in which an ultrasound probe and an image display device are wirelessly connected to each other and a method for controlling the ultrasound system.

2. Description of the Related Art

In the related art, an ultrasound diagnostic apparatus using an ultrasound image has been put to practical use in the medical field. In general, this type of ultrasound diagnostic apparatus includes an ultrasound probe having a transducer array provided therein and an apparatus main body connected to the ultrasound probe. Ultrasonic waves are transmitted from the ultrasound probe to a subject. The ultrasound probe receives ultrasound echoes from the subject. The apparatus main body electrically processes a reception signal to generate an ultrasound image.

In recent years, for example, as disclosed in JP2015-211726A, an ultrasound system has been developed in which an ultrasound probe and an apparatus main body are connected by wireless communication to improve the operability and mobility of the ultrasound probe.

In the wireless ultrasound system, an analog reception signal output from the transducer array of the ultrasound probe is transmitted to the apparatus main body by wireless communication. Alternatively, a circuit for signal processing is provided in the ultrasound probe and the ultrasound probe performs digital processing on the reception signal output from the transducer array and transmits the reception signal to the apparatus main body using wireless communication. The apparatus main body generates an ultrasound image.

SUMMARY OF THE INVENTION

In general, a huge amount of data is acquired by an ultrasound probe in order to generate an ultrasound image. In a case in which the data is wirelessly transmitted from the ultrasound probe to the apparatus main body, it is preferable to adopt a method for compressing the data to reduce communication capacity.

However, the inspection modes for ultrasound diagnosis include an inspection mode, such as a brightness (B) mode in which scanning is completed in units of frames, and an inspection mode, such as a motion (M) mode in which ultrasound images are displayed along the time axis.

In the former inspection mode in which the ultrasound images are displayed in units of frames, a compression process can be performed for each data item corresponding to one frame of the ultrasound image, the data can be wirelessly transmitted from the ultrasound probe to the apparatus main body, and the apparatus main body can display an ultrasound image on the basis of the data restored for each frame.

In contrast, in the latter inspection mode in which the ultrasound images are displayed along the time axis, predetermined separation times are set and data acquired by the ultrasound probe within each separation time is compressed. The compressed data is wirelessly transmitted from the ultrasound probe to the apparatus main body. The apparatus main body generates an ultrasound image on the basis of the data compressed at each separation time. The ultrasound images generated at each separation time are connected along the time axis. Therefore, there is a concern that seams at each separation time will be conspicuous in the ultrasound image and unevenness will occur, which results in the deterioration of the quality of the ultrasound image.

The invention has been made in order to solve the problems of the related art and an object of the invention is to provide an ultrasound system that has an ultrasound probe and an image display device wirelessly connected to each other and can display a high-quality ultrasound image regardless of an inspection mode and a method for controlling the ultrasound system.

In order to achieve the above object, according to the invention, there is provided an ultrasound system comprising an ultrasound probe and an image display device that are wirelessly connected to each other. The ultrasound probe includes: a transducer array; a transmitting and receiving unit that generates a sound ray signal by directing the transducer array to transmit and receive ultrasonic waves; an image information data generation unit that generates image information data on the basis of the sound ray signal generated by the transmitting and receiving unit; a compression unit that compresses the image information data generated by the image information data generation unit; a compression ratio setting unit that sets a compression ratio of the compression unit; and a probe-side wireless communication unit that wirelessly transmits the image information data compressed by the compression unit to the image display device. The image display device includes: a decompression unit that decodes the image information data wirelessly transmitted from the ultrasound probe; a display unit that displays an ultrasound image on the basis of the image information data decoded by the decompression unit; an inspection mode setting unit that sets an inspection mode to be performed among a plurality of predetermined inspection modes; and a display-device-side wireless communication unit that wirelessly transmits a type of the inspection mode set by the inspection mode setting unit to the ultrasound probe. The compression ratio setting unit of the ultrasound probe sets the compression ratio corresponding to the type of the inspection mode wirelessly transmitted from the image display device. The compression unit of the ultrasound probe compresses the image information data on the basis of the compression ratio set by the compression ratio setting unit.

The compression ratio setting unit may set a predetermined first compression ratio in a case in which the type of the inspection mode set by the inspection mode setting unit is a frame unit mode for displaying the ultrasound image in units of frames and may set a second compression ratio lower than the first compression ratio in a case in which the type of the inspection mode set by the inspection mode setting unit is a scroll mode for displaying the ultrasound image in time series.

In this case, preferably, the frame unit mode includes at least one of a brightness mode, a color Doppler mode, or a power Doppler mode, and the scroll mode includes at least one of a motion mode, a pulse Doppler mode, or a continuous wave Doppler mode.

The image display device may further include: an image memory that stores the image information data decoded by the decompression unit; and a storage control unit that controls storage of the image information data in the image memory.

In a case in which the inspection mode set by the inspection mode setting unit is the scroll mode, the display unit may have a scroll display region having a predetermined display length for displaying the ultrasound image generated according to the scroll mode, and the storage control unit may store the image information data in the image memory, using a time width corresponding to the display length as a unit.

Preferably, the image information data is a signal obtained by performing attenuation correction according to a depth of a reflection position of the ultrasonic waves and an envelope detection process on the sound ray signal generated by the transmitting and receiving unit.

Alternatively, the image information data may be an ultrasound image signal obtained by performing attenuation correction according to a depth of a reflection position of the ultrasonic waves and an envelope detection process on the sound ray signal generated by the transmitting and receiving unit and converting the sound ray signal according to a predetermined image display method.

The transmitting and receiving unit may include: a transmitting unit that directs the transducer array to transmit the ultrasonic waves; and a receiving unit that generates the sound ray signal on the basis of a reception signal acquired by the transducer array.

According to the invention, there is provided a method for controlling an ultrasound system including an ultrasound probe and an image display device that are wirelessly connected to each other. The method comprises: setting an inspection mode to be performed among a plurality of predetermined inspection modes in the image display device; wirelessly transmitting a type of the set inspection mode from the image display device to the ultrasound probe; generating a sound ray signal by directing a transducer array of the ultrasound probe to transmit and receive ultrasonic waves; generating image information data on the basis of the generated sound ray signal; compressing the generated image information data at a compression ratio corresponding to the type of the inspection mode set in the image display device; wirelessly transmitting the compressed image information data from the ultrasound probe to the image display device; decoding the image information data wirelessly transmitted from the ultrasound probe in the image display device; and displaying an ultrasound image on a display unit of the image display device on the basis of the decoded image information data.

According to the invention, the compression ratio setting unit of the ultrasound probe sets the compression ratio corresponding to the type of the inspection mode wirelessly transmitted from the image display device, and the compression unit of the ultrasound probe compresses the image information data on the basis of the compression ratio set by the compression ratio setting unit. Therefore, it is possible to display a high-quality ultrasound image regardless of the inspection mode even in a case in which the ultrasound probe and the image display device are wirelessly connected to each other.

DESCRIPTION OF THE PREFERRED EMBODIMENTS

Hereinafter, embodiments of the invention will be described with reference to the accompanying drawings.

Embodiment 1

Figure 1:
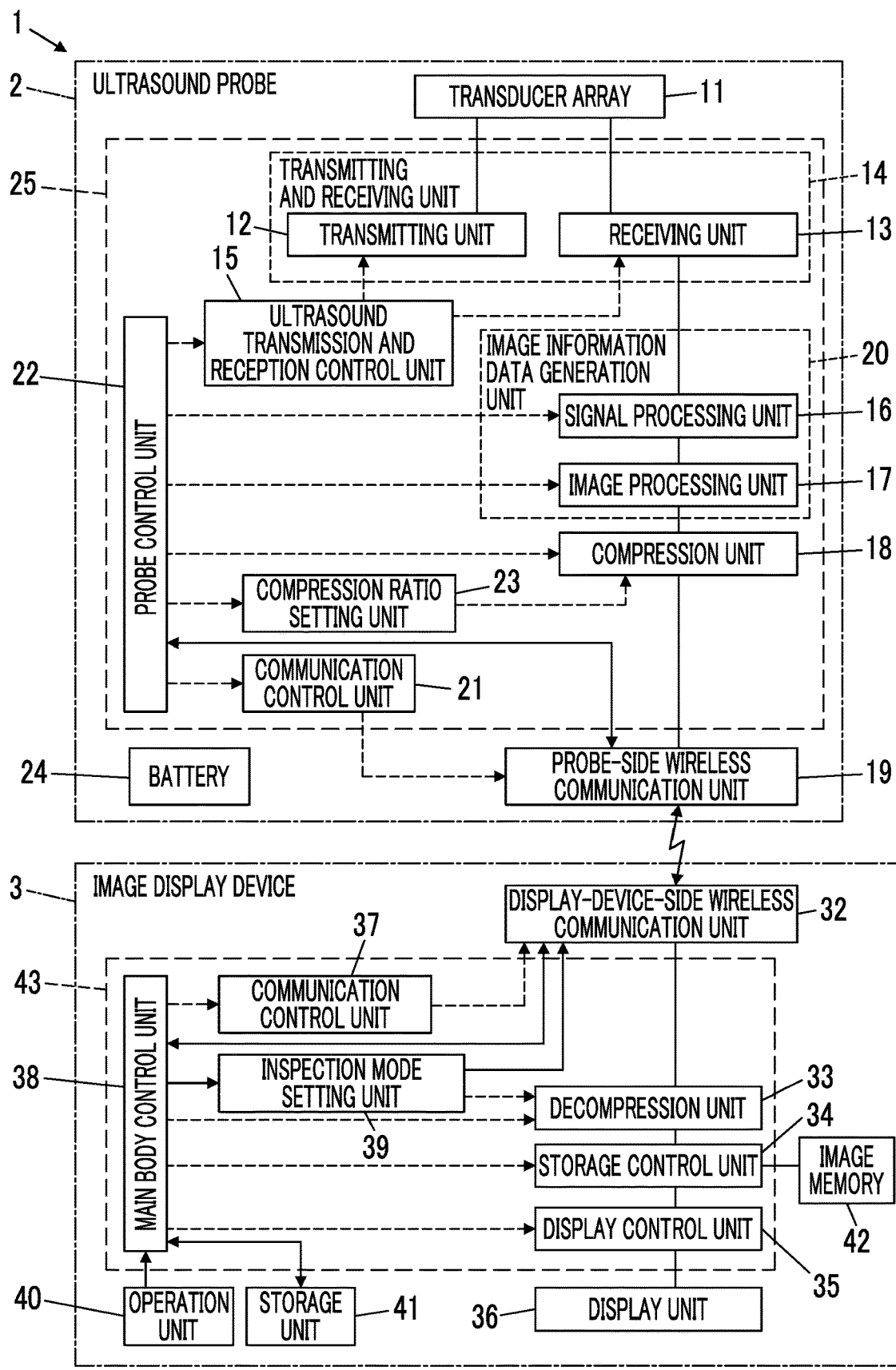
FIG. 1 is a block diagram illustrating a configuration of an ultrasound system according to Embodiment 1 of the invention.

FIG. 1 illustrates the configuration of an ultrasound system 1 according to Embodiment 1 of the invention. The ultrasound system 1 comprises an ultrasound probe 2 and an image display device 3. The ultrasound probe 2 and the image display device 3 are connected to each other by wireless communication.

The ultrasound probe 2 comprises a transducer array 11. The transducer array 11 is connected to a transmitting unit 12 and a receiving unit 13. The transmitting unit 12 and the receiving unit 13 form a transmitting and receiving unit 14. An ultrasound transmission and reception control unit 15 is connected to the transmitting unit 12 and the receiving unit 13. A signal processing unit 16, an image processing unit 17, a compression unit 18, and a probe-side wireless communication unit 19 are sequentially connected to the receiving unit 13. Here, an image information data generation unit 20 is configured by the signal processing unit 16 and the image processing unit 17.

Further, a communication control unit 21 is connected to the probe-side wireless communication unit 19, and a compression ratio setting unit 23 is connected to the compression unit 18. A probe control unit 22 is connected to the ultrasound transmission and reception control unit 15, the signal processing unit 16, the image processing unit 17, the compression unit 18, the probe-side wireless communication unit 19, the communication control unit 21, and the compression ratio setting unit 23. Here, the probe-side wireless communication unit 19 and the probe control unit 22 are connected such that information can be bidirectionally received and transmitted. Further, the ultrasound probe 2 has a battery 24 provided therein.

A probe-side processor 25 is configured by the transmitting and receiving unit 14, the ultrasound transmission and reception control unit 15, the compression unit 18, the image information data generation unit 20, the communication control unit 21, the probe control unit 22, and the compression ratio setting unit 23.

The image display device 3 includes a display-device-side wireless communication unit 32. A decompression unit 33, a storage control unit 34, a display control unit 35, and a display unit 36 are sequentially connected to the display-device-side wireless communication unit 32. A communication control unit 37 and an inspection mode setting unit 39 are connected to the display-device-side wireless communication unit 32. The inspection mode setting unit 39 is connected to the decompression unit 33. An image memory 42 is connected to the storage control unit 34.

Further, a main body control unit 38 is connected to the display-device-side wireless communication unit 32, the decompression unit 33, the storage control unit 34, the display control unit 35, the communication control unit 37, and the inspection mode setting unit 39. An operation unit 40 and a storage unit 41 are connected to the main body control unit 38. The display-device-side wireless communication unit 32 and the main body control unit 38 are connected such that information can be bidirectionally received and transmitted. The main body control unit 38 and the storage unit 41 are connected such that information can be bidirectionally received and transmitted.

Furthermore, the decompression unit 33, the storage control unit 34, the display control unit 35, the communication control unit 37, the main body control unit 38, and the inspection mode setting unit 39 form a display-device-side processor 43.

The transducer array 11 of the ultrasound probe 2 has a plurality of ultrasound transducers which are arranged one-dimensionally or two-dimensionally. Each of the transducers transmits ultrasonic waves according to a driving signal supplied from the transmitting unit 12, receives waves reflected from a subject, and outputs an analog reception signal. Each transducer is configured using an element in which electrodes are formed at both ends of a piezoelectric body consisting of, for example, a piezoelectric ceramic typified by lead zirconate titanate (PZT), a polymeric piezoelectric element typified by polyvinylidene difluoride (PVDF), or a piezoelectric single crystal typified by lead magnesium niobate-lead titanate (PMN-PT).

The ultrasound transmission and reception control unit 15 controls the transmitting unit 12 and the receiving unit 13 of the transmitting and receiving unit 14 such that the transmission of ultrasound beams and the reception of ultrasound echoes are performed on the basis of an inspection mode, a scanning method, and a predetermined transmission and reception sequence which have been set by the inspection mode setting unit 39 of the display-device-side processor 43 and instructed by the probe control unit 22. Here, for example, a brightness (B) mode which is a frame unit mode for displaying ultrasound images in units of frames and a motion (M) mode which is a scroll mode for displaying ultrasound images in time series are used as the inspection mode. For example, any one of an electronic sector scanning method, an electronic linear scanning method, or an electronic convex scanning method is used as the scanning method.

The transmitting unit 12 of the transmitting and receiving unit 14 includes, for example, a plurality of pulse generators, adjusts the amount of delay of each driving signal on the basis of a transmission delay pattern selected according to a control signal from the ultrasound transmission and reception control unit 15 such that the ultrasonic waves transmitted from the plurality of transducers of the transducer array 11 form an ultrasound beam, and supplies the driving signals to the plurality of transducers. As such, in a case in which a pulsed or continuous-wave voltage is applied to the electrodes of the transducers of the transducer array 11, the piezoelectric body is expanded and contracted and pulsed or continuous ultrasonic waves are generated from each transducer. An ultrasound beam whose focus has been narrowed down on a certain scanning line is formed from a combined wave of the ultrasonic waves.

The transmitted ultrasound beam is reflected by a target, such as a part of the subject, and is propagated as a so-called ultrasound echo toward the transducer array 11. The ultrasound echoes propagated toward the transducer array 11 in this way are received by each of the ultrasound transducers forming the transducer array 11. In this case, each of the ultrasound transducers forming the transducer array 11 receives the propagated ultrasound echoes, is expanded and contracted to generate an electric signal, and outputs the electric signal to the receiving unit 13.

Figure 2:
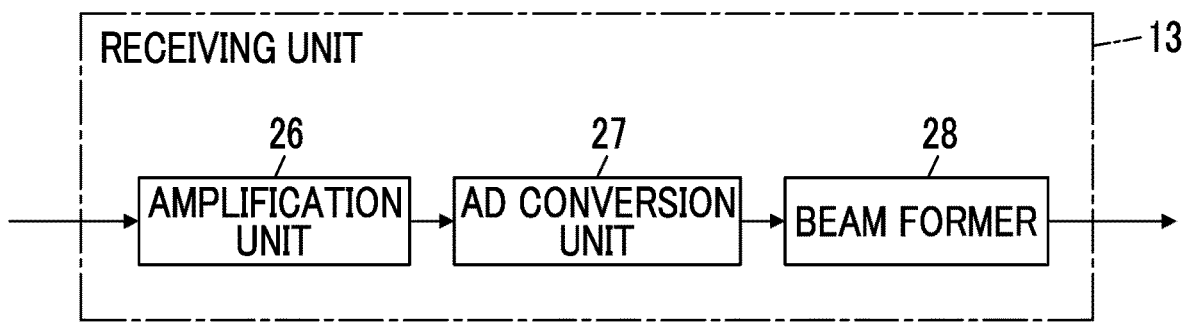
FIG. 2 is a block diagram illustrating an internal configuration of a receiving unit according to Embodiment 1 of the invention.

The receiving unit 13 of the transmitting and receiving unit 14 processes the reception signal output from the transducer array 11 according to a control signal from the ultrasound transmission and reception control unit 15. As illustrated in FIG. 2, the receiving unit 13 has a configuration in which an amplification unit 26, an analog digital (AD) conversion unit 27, and a beam former 28 are connected in series to each other. The amplification unit 26 amplifies the reception signal which is an analog signal input from each of the ultrasound transducers forming the transducer array 11 and transmits the amplified reception signal to the AD conversion unit 27. The AD conversion unit 27 converts the analog reception signal transmitted from the amplification unit 26 into a digital signal to acquire reception data, and transmits the reception data to the beam former 28. The beam former 28 performs a reception focusing process which gives a delay to each reception data item following the set sound velocity on the basis of a reception delay pattern selected according to a control signal from the ultrasound transmission and reception control unit 15 and performs addition (phasing addition). The sound ray signal in which the focus of the ultrasound echo is narrowed down on a certain scanning line is generated by the reception focusing process.

The image information data generation unit 20 of the probe-side processor 25 generates image information data on the basis of the sound ray signal generated by the beam former 28 of the receiving unit 13.

Figure 3:
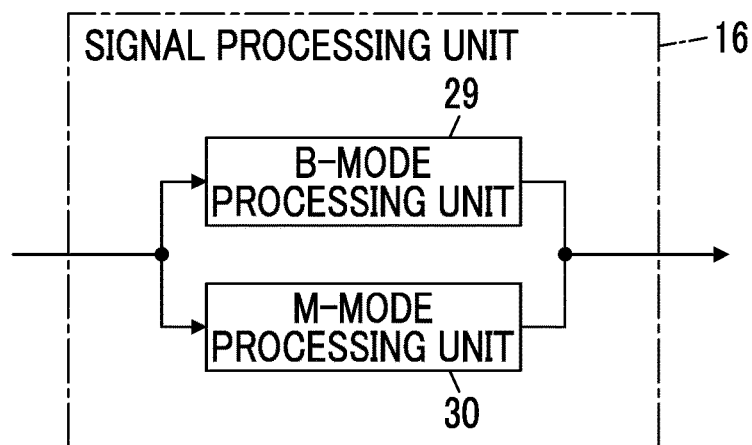
FIG. 3 is a block diagram illustrating an internal configuration of a signal processing unit according to Embodiment 1 of the invention.

Here, the signal processing unit 16 of the image information data generation unit 20 includes a B-mode processing unit 29 and an M-mode processing unit 30 as illustrated in FIG. 3 and performs signal processing on the sound ray signal generated by the beam former 28 of the receiving unit 13, selectively using the B-mode processing unit 29 and the M-mode processing unit 30, under the control of the probe control unit 22.

The B-mode processing unit 29 of the signal processing unit 16 corrects the attenuation of the sound ray signal generated by the beam former 28 of the receiving unit 13 caused by a propagation distance according to the depth of the position where the ultrasonic waves are reflected and performs an envelope detection process on the sound ray signal to generate a signal which is tomographic image information related to the tissues in the subject.

The M-mode processing unit 30 of the signal processing unit 16 plots signal intensity in the depth direction along a set scanning line on the time axis and generates a signal indicating a time-series change in the tissues of the subject.

The image processing unit 17 of the image information data generation unit 20 raster-converts the signal generated by the B-mode processing unit 29 and the signal generated by the M-mode processing unit 30 of the signal processing unit 16 into image signals following a general television signal scanning method and performs various kinds of necessary image processing, such as brightness correction, gradation correction, sharpness correction, and color correction, to generate a B-mode image signal corresponding to a tomographic image of the tissues of the subject and an M-mode image signal corresponding to an image indicating a time-series change in the tissues of the subject, which are ultrasound image signals, as image information data.

The compression unit 18 of the probe-side processor 25 compresses the B-mode image signal and the M-mode image signal generated by the image information data generation unit 20 on the basis of the compression ratio set by the compression ratio setting unit 23 of the probe-side processor 25, using a predetermined compression format. In this case, the compression unit 18 compresses the B-mode image signal and the M-mode image signal as two-dimensional data. Here, the M-mode image signal is data that is continuous in time series. Unlike the B-mode image signal, since the M-mode image signal is not separated in units of frames, the compression unit 18 divides and compresses the M-mode image signal at an interval of a predetermined separation time. For example, a time interval of 16 ms and 33 ms is used as the predetermined separation time.

In addition, the compression unit 18 can use, for example, so-called Joint-Photographic-Experts-Group (JPEG) as the predetermined compression format. For example, in JPEG, an image signal is compressed as follows: the image signal is divided into a plurality of blocks corresponding to a predetermined size; and conversion into a frequency domain, such as Fourier transform, a reduction in the amount of data by quantization and entropy coding, and conversion from the frequency domain into a spatial domain are performed on each of the divided blocks.

Specifically, the accuracy of the intensity of a frequency component is reduced by quantization in the image signal converted into the frequency domain, and data indicating a plurality of pixels forming the image signal is replaced with data indicating a smaller number of pixels. A shorter bit string is allocated to frequency components which are more abundant in the quantized image signal by entropy coding. Then, the entropy-coded image signal is converted from the frequency domain to the spatial domain. In the quantization, for example, among the data items indicating a plurality of pixels forming the image signal, a predetermined number of data items at positions close to each other is divided as a cluster. Signal intensity in those clusters is averaged to reduce the amount of data in the image signal. In this way, for example, the B-mode image signal and the M-mode image signal compressed by JPEG are generated.

The compression ratio setting unit 23 of the probe-side processor 25 sets the compression ratios of the B-mode image signal and the M-mode image signal in the compression unit 18. The compression ratio setting unit 23 sets the compression ratio according to whether the inspection mode set by the inspection mode setting unit 39 of the image display device 3 is the frame unit mode or the scroll mode, which will be described below. Specifically, the compression ratio setting unit 23 sets a compression ratio corresponding to the B-mode in a case in which the inspection mode setting unit 39 sets the B-mode which is the frame unit mode and sets a compression ratio corresponding to the M-mode in a case in which the inspection mode setting unit 39 sets the M-mode which is the scroll mode. In this case, the compression ratio setting unit 23 sets the compression ratios such that the compression ratio corresponding to the B-mode and the compression ratio corresponding to the M-mode are different from each other.

The probe-side wireless communication unit 19 of the ultrasound probe 2 includes an antenna for transmitting and receiving radio waves, modulates a carrier on the basis of the B-mode image signal which has been compressed in units of frames by the compression unit 18 and the M-mode image signal which has been divided and compressed at an interval of the predetermined separation time by the compression unit 18 to generate transmission signals indicating the B-mode image signal and the M-mode image signal, supplies the generated transmission signals to the antenna, and transmits radio waves from the antenna to wirelessly transmit the B-mode image signal and the M-mode image signal in sequence. For example, amplitude shift keying (ASK), phase shift keying (PSK), quadrature phase shift keying (QPSK), and 16 quadrature amplitude modulation (16QAM) can be used as the carrier modulation method.

Further, the probe-side wireless communication unit 19 receives a transmission signal indicating the inspection mode set by the inspection mode setting unit 39, which will be described below, from the display-device-side wireless communication unit 32 of the image display device 3, demodulates the received transmission signal, and outputs information indicating the inspection mode to the probe control unit 22. The information indicating the inspection mode is output from the probe control unit 22 to the ultrasound transmission and reception control unit 15 and the compression ratio setting unit 23.

The communication control unit 21 of the probe-side processor 25 controls the probe-side wireless communication unit 19 such that the B-mode image signal and the M-mode image signal are transmitted with transmission radio field intensity set by the probe control unit 22. Further, the communication control unit 21 of the probe-side processor 25 controls the probe-side wireless communication unit 19 such that the information indicating the inspection mode is received from the display-device-side wireless communication unit 32 of the image display device 3.

The probe control unit 22 of the probe-side processor 25 controls each unit of the ultrasound probe 2 on the basis of, for example, a program stored in advance.

The battery 24 of the ultrasound probe 2 is provided in the ultrasound probe 2 and supplies power to each circuit of the ultrasound probe 2.

The display-device-side wireless communication unit 32 of the image display device 3 includes an antenna for transmitting and receiving radio waves, receives the transmission signals indicating the B-mode image signal and the M-mode image signal transmitted by the probe-side wireless communication unit 19 of the ultrasound probe 2 through the antenna, demodulates the received transmission signals, and outputs the B-mode image signal compressed in units of frames and the M-mode image signal divided and compressed at an interval of the predetermined separation time. Further, the display-device-side wireless communication unit 32 modulates the carrier on the basis of the information indicating the inspection mode set by the inspection mode setting unit 39 to generate a transmission signal indicating the inspection mode and wirelessly transmits the generated transmission signal to the probe-side wireless communication unit 19 of the ultrasound probe 2. For example, ASK, PSK, QPSK, and 16QAM are used as the carrier modulation method, similarly to the modulation method in the probe-side wireless communication unit 19.

The communication control unit 37 of the display-device-side processor 43 controls the display-device-side wireless communication unit 32 of the image display device 3 such that the transmission signals indicating the B-mode image signal and the M-mode image signal are received from the probe-side wireless communication unit 19 of the ultrasound probe 2. Further, the communication control unit 37 of the display-device-side processor 43 controls the display-device-side wireless communication unit 32 such that the information indicating the inspection mode set by the inspection mode setting unit 39 is transmitted with the transmission radio field intensity set by the main body control unit 38.

The inspection mode setting unit 39 of the display-device-side processor 43 sets, as the inspection mode, one of the B-mode and the M-mode which is to be performed in the diagnosis. In this case, for example, the inspection mode setting unit 39 can set an inspection mode selected by the user through the operation unit 40 of the image display device 3 as the inspection mode to be performed in the diagnosis.

The decompression unit 33 of the display-device-side processor 43 decodes the compressed B-mode image signal and M-mode image signal output by the display-device-side wireless communication unit 32 of the image display device 3 on the basis of the inspection mode set by the inspection mode setting unit 39 and the compression format used.

The storage control unit 34 of the display-device-side processor 43 controls the image memory 42 such that the B-mode image signal and the M-mode image signal decoded by the decompression unit 33 are stored in the image memory 42.

Under the control of the main body control unit 38, the display control unit 35 of the display-device-side processor 43 performs a predetermined process on the B-mode image signal and the M-mode image signal stored in the image memory 42 and displays a B-mode image based on the B-mode image signal and an M-mode image based on the M-mode image signal on the display unit 36. In this case, the M-mode image which is an image corresponding to the scroll mode is displayed such that the M-mode images divided at an interval of the predetermined separation time are connected to each other.

The main body control unit 38 of the display-device-side processor 43 controls each unit of the image display device 3 on the basis of the program stored in advance in the storage unit 41 and the operation of the user input through the operation unit 40.

The display unit 36 of the image display device 3 displays images, such as the B-mode image and the M-mode images, under the control of the display control unit 35, and includes, for example, a display device such as a liquid crystal display (LCD).

The operation unit 40 of the image display device 3 is used by the user to perform an input operation and can be configured to comprise, for example, a keyboard, a mouse, a trackball, a touch pad, and a touch panel.

The storage unit 41 stores, for example, an operation program for the image display device 3. The following can be used as the storage unit 41: a recording medium, such as a flash memory, a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory); or a sever.

Here, the probe-side processor 25 including the transmitting unit 12, the receiving unit 13, the ultrasound transmission and reception control unit 15, the signal processing unit 16, the image processing unit 17, the compression unit 18, the communication control unit 21, the probe control unit 22, and the compression ratio setting unit 23 in the ultrasound probe 2 and the display-device-side processor 43 including the storage control unit 34, the display control unit 35, the communication control unit 37, the main body control unit 38, and the inspection mode setting unit 39 in the image display device 3 are implemented by a central processing unit (CPU) and a control program for causing the CPU to perform various processes. However, the processors may be implemented by a field programmable gate array (FPGA), a digital signal processor (DSP), an application specific integrated circuit (ASIC), a graphics processing unit (GPU), other integrated circuits (ICs), or combinations thereof.

The image memory 42 of the image display device 3 stores the B-mode image signal and the M-mode image signal decoded by the decompression unit 33 under the control of the storage control unit 34 of the display-device-side processor 43. Similarly to the storage unit 41, for example, the following can be used as the image memory 42: a recording medium, such as a flash memory, an HDD, an SSD, an FD, an MO disc, an MT, a RAM, a CD, a DVD, an SD card, or a USB memory; or a server.

Some or all of the transmitting unit 12, the receiving unit 13, the ultrasound transmission and reception control unit 15, the signal processing unit 16, the image processing unit 17, the compression unit 18, the communication control unit 21, the probe control unit 22, and the compression ratio setting unit 23 of the probe-side processor 25 may be integrated into, for example, one CPU. Similarly, some or all of the storage control unit 34, the display control unit 35, the communication control unit 37, the main body control unit 38, and the inspection mode setting unit 39 of the display-device-side processor 43 may be integrated into, for example, one CPU.

Next, the operation of the ultrasound system 1 according to Embodiment 1 of the invention will be described.

First, in the image display device 3, the inspection mode setting unit 39 of the display-device-side processor 43 sets one of the B-mode and the M-mode as the inspection mode used for diagnosis. In this case, for example, the inspection mode setting unit 39 can set the inspection mode selected by the user through the operation unit 40 of the image display device 3 as the inspection mode used for diagnosis.

In a case in which the inspection mode used for diagnosis is set in this way, the display-device-side wireless communication unit 32 of the image display device 3 modulates a carrier on the basis of information indicating the inspection mode set by the inspection mode setting unit 39 to generate a transmission signal indicating the inspection mode and wirelessly transmits the generated transmission signal to the probe-side wireless communication unit 19 of the ultrasound probe 2. The transmission signal indicating the inspection mode, which has been wirelessly transmitted from the display-device-side wireless communication unit 32 in this way, is demodulated into the information indicating the inspection mode by the probe-side wireless communication unit 19 and is transmitted to the probe control unit 22 of the probe-side processor 25. The probe control unit 22 transmits the information indicating the inspection mode to the ultrasound transmission and reception control unit 15, the compression unit 18, and the compression ratio setting unit 23.

The ultrasound transmission and reception control unit 15 of the probe-side processor 25 controls the transmitting and receiving unit 14 on the basis of the information indicating the inspection mode transmitted from the probe control unit 22 such that ultrasonic waves are transmitted and received in the transducer array 11. In this case, first, ultrasound beams are transmitted from the plurality of ultrasound transducers of the transducer array 11 according to a driving signal from the transmitting unit 12 of the transmitting and receiving unit 14 under the control of the ultrasound transmission and reception control unit 15. Ultrasound echoes from the subject, which are based on the transmitted ultrasound beams, are received by each ultrasound transducer and a reception signal which is an analog signal is output to the receiving unit 13, is amplified by the amplification unit 26, and is converted by the AD conversion unit 27. As a result, reception data is acquired. The beam former 28 performs the reception focusing process on the reception data to generate a sound ray signal corresponding to each frame of the ultrasound image.

The signal processing unit 16 of the image information data generation unit 20 performs predetermined signal processing on the sound ray signal generated by the beam former 28 of the receiving unit 13 to obtain a signal indicating a tomographic image of the tissues of the subject or a signal indicating a time-series change in the tissues of the subject. In this case, the signal processing unit 16 generates the signal indicating the tomographic image and the signal indicating the time-series change in the tissues of the subject on the basis of the inspection mode set by the inspection mode setting unit 39 of the display-device-side processor 43.

For example, in a case in which the inspection mode setting unit 39 sets the B-mode as the inspection mode used for diagnosis, the B-mode processing unit 29 of the signal processing unit 16 performs attenuation correction according to the depth of a reflection position and an envelope detection process on the sound ray signal to generate a signal indicating the tomographic image of the tissues of the subject under the control of the probe control unit 22 of the probe-side processor 25. Further, for example, in a case in which the inspection mode setting unit 39 sets the M-mode as the inspection mode used for diagnosis, the B-mode processing unit 29 generates a signal indicating the tomographic image of the tissues of the subject and the M-mode processing unit 30 of the signal processing unit 16 plots signal intensity in the depth direction along the set scanning line on the time axis to generate a signal indicating a time-series change in the tissues of the subject, under the control of the probe control unit 22.

The image processing unit 17 raster-converts the signal generated by the B-mode processing unit 29 and the signal generated by the M-mode processing unit 30 of the signal processing unit 16 into image signals following a general television signal scanning method. Then, various kinds of necessary image processing, such as brightness correction, gradation correction, sharpness correction, and color correction, are performed on the image signals to generate a B-mode image signal and an M-mode image signal.

Further, the compression ratio setting unit 23 of the probe-side processor 25 sets compression ratios for compressing the B-mode image signal and the M-mode image signal on the basis of the information indicating the inspection mode transmitted from the probe control unit 22. For example, the compression ratio setting unit 23 sets different compression ratios for the B-mode image signal and the M-mode image signal.

Figure 4:
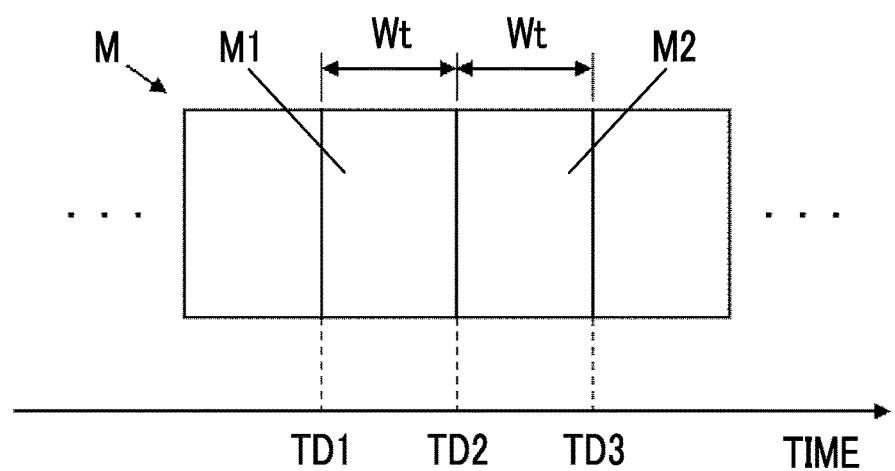
FIG. 4 is a diagram schematically illustrating an M-mode image signal divided at an interval of a predetermined separation time.

Here, the M-mode image signal corresponding to the scroll mode for displaying ultrasound images in time series is not separated in units of frames unlike the B-mode image signal corresponding to the frame unit mode for displaying ultrasound images in units of frames. Therefore, for example, as illustrated in FIG. 4, the M-mode image is divided at an interval of a predetermined separation time Wt, is compressed, and is wirelessly transmitted. Then, the M-mode images divided at an interval of the separation time Wt are displayed so as to be connected to each other. In the example illustrated in FIG. 4, an M-mode image signal M which is continuous in time is divided at times TD1, TD2, and TD3 at an interval of the predetermined separation time Wt and M-mode image signals M1 and M2 corresponding to the separation times Wt are generated.

In a case in which each of the divided M-mode image signals is compressed in a format such as JPEG, for example, so-called quantization is performed on the M-mode image signal to reduce the amount of data of the M-mode image signal. In the quantization, for example, a predetermined number of data items at positions close to each other among data items indicating a plurality of pixels forming the M-mode image signal are divided as a cluster, and the intensity of the M-mode image signal in the clusters is averaged. In this case, as the compression ratio of the M-mode image signal becomes higher, the number of data items forming the cluster in the M-mode image signal becomes larger. As a result, the amount of data is further reduced. Therefore, in a central portion of the M-mode image signal and in the end portions divided at an interval of the separation time Wt, particularly, as the compression ratio becomes higher, a difference in the number of data items forming the cluster becomes larger. Therefore, different quantization processes are performed in the central portion and the end portion.

Therefore, for example, in the M-mode image signal M1 illustrated in FIG. 4, different quantization processes are performed in the central portion and the end portion, that is, portions near the times TD1 and TD2. In addition, in the M-mode image signal M2 adjacent to the M-mode image signal M1, different quantization processes are performed in the central portion and the end portion, that is, portions near the times TD2 and TD3. Further, different quantization processes are performed in a portion near the time TD2 in the M-mode image signal M1 and a portion near the time TD2 in the M-mode image signal M2. As a result, there is a concern that, as the compression ratio used to compress the M-mode image signal becomes higher, the difference between the intensity of the M-mode image signal M1 near the time TD2 and the intensity of the M-mode image signal M2 near the time TD2, that is, intensity unevenness will become larger. The intensity unevenness causes unevenness to occur at each separation time Wt in the M-mode image displayed on the display unit 36.

Therefore, for example, the compression ratio setting unit 23 of the probe-side processor 25 can set the compression ratio of the B-mode image signal to a first compression ratio and set the compression ratio of the M-mode image signal to a second compression ratio lower than the first compression ratio. As such, the compression ratio setting unit 23 sets the compression ratio of the M-mode image signal corresponding to the scroll mode so as to be reduced. Therefore, it is possible to suppress the occurrence of the intensity unevenness of the M-mode image signal at the predetermined separation time Wt.

The compression unit 18 of the probe-side processor 25 compresses the B-mode image signal and the M-mode image signal generated by the image processing unit 17 of the image information data generation unit 20, using the compression ratio set by the compression ratio setting unit 23 and a predetermined compression format, on the basis of the information indicating the inspection mode transmitted from the probe control unit 22. In this case, for the M-mode image signal corresponding to the scroll mode, compression is performed on the signals divided at an interval of the predetermined separation time Wt. Here, for example, a time interval of 16 ms and 33 ms is used as the predetermined separation time Wt.

For the B-mode image signal and the M-mode image signal compressed by the compression unit 18, under the control of the communication control unit 21, a carrier is modulated on the basis of the B-mode image signal compressed in units of frames and the M-mode image signal divided and compressed at an interval of the predetermined separation time Wt to generate transmission signals indicating the B-mode image signal and the M-mode image signal, and the generated transmission signals are wirelessly transmitted to the display-device-side wireless communication unit 32 of the image display device 3.

The transmission signals indicating the B-mode image signal and the M-mode image signal wirelessly transmitted from the probe-side wireless communication unit 19 of the ultrasound probe 2 are received by the display-device-side wireless communication unit 32 of the image display device 3, are demodulated, and are output as the B-mode image signal compressed in units of frames and the M-mode image signal divided and compressed at an interval of the predetermined separation time Wt, respectively.

The B-mode image signal and the M-mode image signal output by the display-device-side wireless communication unit 32 are decoded by the decompression unit 33 under the control of the main body control unit 38 of the display-device-side processor 43, and are stored in the image memory 42 under the control of the storage control unit 34 of the display-device-side processor 43. In a case in which the inspection mode set by the inspection mode setting unit 39 of the display-device-side processor 43 is the M-mode, the storage control unit 34 stores, in the image memory 42, the M-mode image signals that are continuous in time from an M-mode image signal corresponding to the latest separation time Wt output from the decompression unit 33 to an M-mode image signal corresponding to the separation time Wt that is older by a predetermined time.

Figure 5:
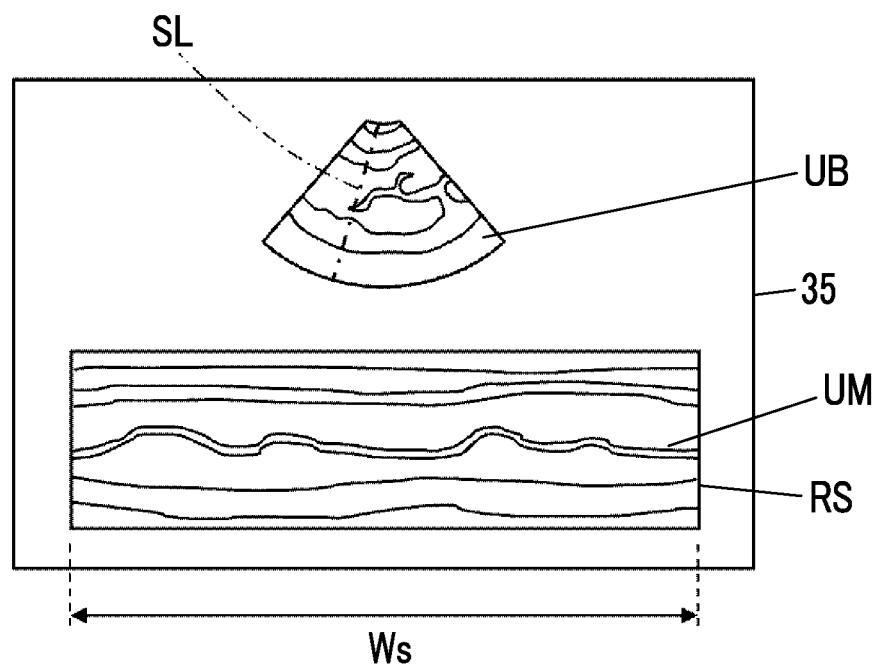
FIG. 5 is a diagram schematically illustrating an example of the display of a B-mode image and an M-mode image.

The B-mode image signal and the M-mode image signal stored in the image memory 42 are subjected to a predetermined process by the display control unit 35 of the display-device-side processor 43 and are displayed as a B-mode image and an M-mode image on the display unit 36 of the image display device 3. In a case in which the M-mode is set as the inspection mode by the inspection mode setting unit 39, for example, a B-mode image UB and an M-mode image UM are displayed on the display unit 36 as illustrated in FIG. 5. In the example illustrated in FIG. 5, the B-mode image UB is displayed on the display unit 36 and a scanning line SL is displayed so as to be superimposed on the B-mode image UB. For example, the scanning line SL is selected by the user through the operation unit 40 of the image display device 3. In addition, the display unit 36 has a scroll display region RS having a determined display length Ws. The M-mode image UM on the scanning line SL which is displayed so as to be superimposed on the B-mode image UB is displayed in the scroll display region RS.

Figure 6:
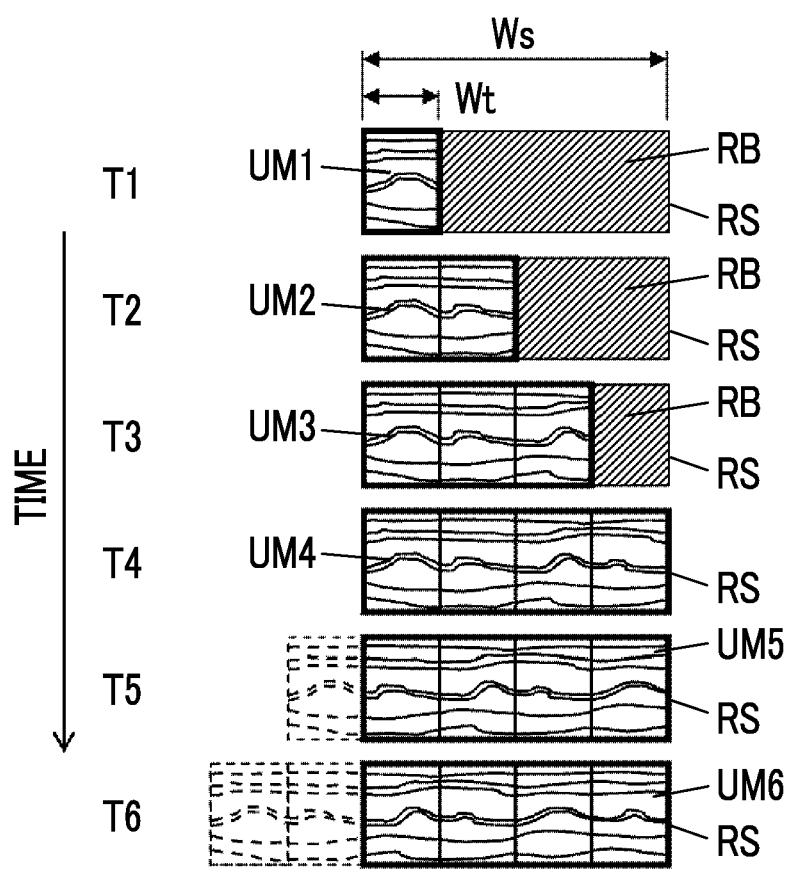
FIG. 6 is a diagram schematically illustrating a change in the M-mode image displayed on the display unit over time in Embodiment 1 of the invention.

Here, the M-mode image signal which is an image signal corresponding to the scroll mode is divided and compressed at an interval of the predetermined separation time Wt and is wirelessly transmitted from the ultrasound probe 2 to the image display device 3 in sequence. Therefore, for example, in the scroll display region RS of the display unit 36, the M-mode images UM are sequentially displayed on the display unit 36 as illustrated in FIG. 6. FIG. 6 illustrates an example in which the display length Ws of the scroll display region RS is four times as long as the predetermined separation time Wt.

First, at a time T1, an M-mode image UM1 having a time length equal to the predetermined separation time Wt is displayed in the scroll display region RS. In the remaining portion of the scroll display region RS, the M-mode image UM1 is not displayed and a black region RB is displayed.

Then, at a time T2, an M-mode image UM2 having a time length that is twice the separation time Wt as a whole is displayed in the scroll display region RS. In the remaining portion of the scroll display region RS, the M-mode image UM2 is not displayed and the black region RB is displayed. Here, in the scroll display region RS, images having a width corresponding to the separation time Wt are displayed so as to be connected to each other. The compression ratio setting unit 23 of the probe-side processor 25 sets a compression ratio corresponding to the M-mode, and the compression unit 18 of the probe-side processor 25 compresses the M-mode image signal using the set compression ratio. Therefore, unevenness at each separation time Wt in the M-mode image UM2 is inconspicuous.

At a time T3, an M-mode image UM3 having a time length that is three times as long as the separation time Wt as a whole is displayed in the scroll display region RS. In the remaining portion of the scroll display region RS, the M-mode image UM3 is not displayed and the black region RB is displayed.

At a time T4, an M-mode image UM4 having a time length that is four times as long as the separation time Wt as a whole is displayed in the scroll display region RS and the black region RB is not displayed. As such, in a case in which the time length of the acquired M-mode image is less than the display length Ws of the scroll display region RS, the black region RB is displayed in a region in which the M-mode image is not displayed in the scroll display region RS. In a case in which the time length of the acquired M-mode image is equal to the display length Ws of the scroll display region RS, the black region RB is not displayed.

At a time T5, an M-mode image UM5 having a time length that is five times as long as the separation time Wt as a whole is acquired. In the M-mode image UM5, only a portion having a display length Ws which is a time length that is four times as long as the separation time Wt is displayed in the scroll display region RS of the display unit 36. For example, in the M-mode image UM5, the latest image corresponding to the display length Ws is displayed in the scroll display region RS. In this case, for example, the entire M-mode image UM5 can be displayed so as to be scrolled in the scroll display region RS by the operation of the user input through the operation unit 40.

Further, at a time T6, an M-mode image UM6 having a time length that is six times as long as the separation time Wt as a whole is acquired. As in the case at the time T5, in the M-mode image UM6, only a portion having the display length Ws is displayed in the scroll display region RS of the display unit 36. For example, in the M-mode image UM6, the latest image corresponding to the display length Ws is displayed in the scroll display region RS. In this case, the entire M-mode image UM6 can be displayed so as to be scrolled in the scroll display region RS by the operation of the user input through the operation unit 40.

In this way, the M-mode images are sequentially displayed in the scroll display region RS of the display unit 36.

As described above, according to the ultrasound system 1 of Embodiment 1 of the invention, the compression ratio setting unit 23 of the probe-side processor 25 sets a compression ratio corresponding to the inspection mode set by the inspection mode setting unit 39 of the display-device-side processor 43, and the compression unit 18 divides and compresses the M-mode image signal, which is a signal corresponding to the scroll mode, at an interval of the predetermined separation time Wt, using the set compression ratio. Therefore, in a case in which the M-mode image is displayed on the display unit 36, unevenness at each predetermined separation time Wt is suppressed. Therefore, it is possible to display a high-quality ultrasound image, regardless of the inspection mode, while wirelessly connecting the ultrasound probe 2 and the image display device 3.

In Embodiment 1, in a case in which the time length of the acquired M-mode image is less than the display length Ws of the scroll display region RS, the black region RB is displayed in the region in which the M-mode image is not displayed. However, a method for displaying the region in which the M-mode image is not displayed is not limited thereto. For example, in the scroll display region RS, the black region RB may not be displayed in the region in which the M-mode image is not displayed and the region may be blank.

In addition, for the M-mode image signal corresponding to the scroll mode signal, the storage control unit 34 of the display-device-side processor 43 stores, in the image memory 42, the M-mode image signals that are continuous from the M-mode image signal corresponding to the latest separation time Wt to the M-mode image signal corresponding to the separation time Wt that is older by a predetermined time. Further, the storage control unit 34 can store the M-mode image signal in the image memory 42, using a time width corresponding to the display length Ws of the scroll display region RS of the display unit 36 as a unit.

Figure 7:
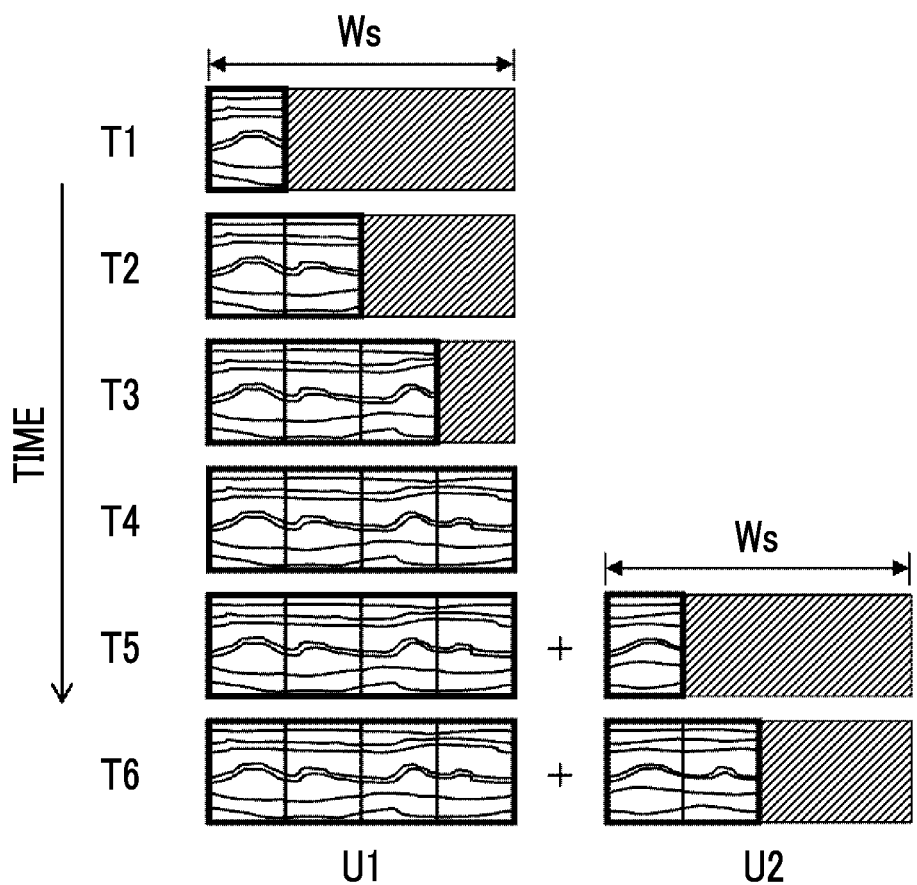
FIG. 7 is a diagram schematically illustrating a change in the M-mode image signal stored in an image memory over time in Embodiment 1 of the invention.

For example, as illustrated in FIG. 7, until the cumulative time width of the M-mode image signals output from the display-device-side wireless communication unit 32 of the image display device 3 reaches a time width corresponding to the display length Ws of the scroll display region RS, the storage control unit 34 can store the M-mode image signal in a first unit of storage U1 that corresponds to the time width corresponding to the display length Ws of the scroll display region RS. Further, in a case in which the cumulative time width of the M-mode image signals output from the decompression unit 33 of the display-device-side processor 43 is greater than the time width corresponding to the display length Ws of the scroll display region RS, the storage control unit 34 can sequentially store the M-mode image signals in the subsequent unit of storage such as a second unit of storage U2.

In this case, for example, as illustrated in FIG. 7, the display control unit 35 of the display-device-side processor 43 displays the M-mode image on the display unit 36 on the basis of the M-mode image signal for each unit of storage stored in the image memory 42. That is, the display control unit 35 displays the M-mode image on the display unit 36 on the basis of the M-mode image signal of the first unit of storage from the time T1 to the time T4. At the time T5 and the time T6, the display control unit 35 displays the M-mode images on the display unit 36 on the basis of the M-mode image signal of the first unit of storage and the M-mode image signal of the next unit of storage.

In Embodiment 1, the case in which the B-mode is used as the frame unit mode and the M-mode is used as the scroll mode has been described. However, the inspection mode used as the frame unit mode and the scroll mode is not limited thereto. For example, in addition to the B-mode, a color Doppler (CF) mode and a power Doppler (PD) mode can be used as the frame unit mode. In addition to the M-mode, for example, a pulse Doppler (PW) mode, and a continuous wave Doppler (CW) mode can be used as the scroll mode. In this case, for example, these inspection modes can be used by providing a Doppler processing unit that performs a quadrature detection process on the sound ray signal in the signal processing unit 16 of the image information data generation unit 20, which is not illustrated.

Further, in this case, the inspection mode setting unit 39 of the display-device-side processor 43 can set an inspection mode used for diagnosis among the above-described plurality of inspection modes.

In addition, in this case, the compression ratio setting unit 23 of the probe-side processor 25 can set the compression ratio of the image information data according to whether the inspection mode set by the inspection mode setting unit 39 is the frame unit mode or the scroll mode. Furthermore, the compression ratio setting unit 23 can set different predetermined compression ratios according to the type of the inspection mode set by the inspection mode setting unit 39 among the above-described plurality of inspection modes.

Embodiment 2

Figure 8:
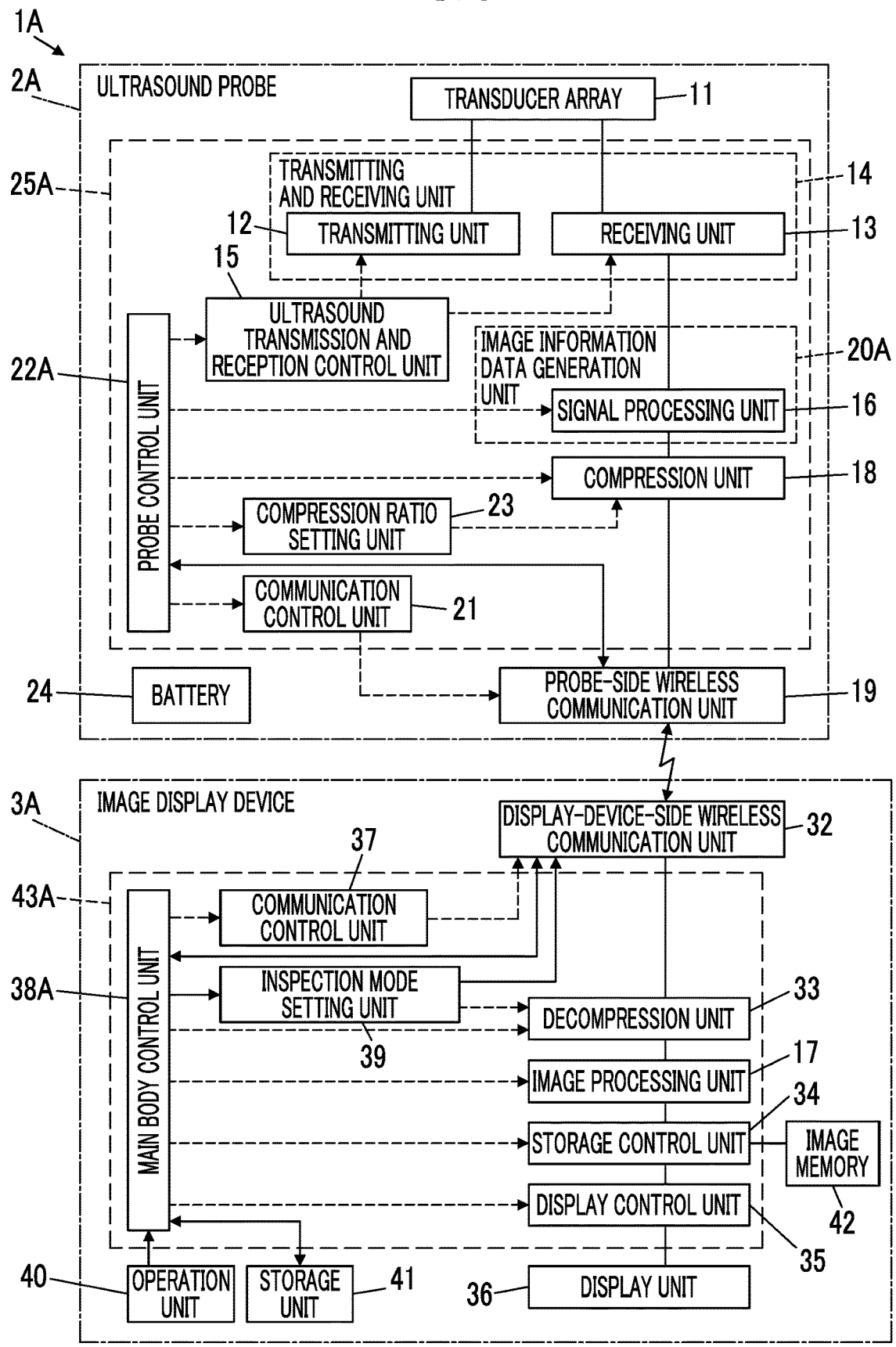
FIG. 8 is a block diagram illustrating a configuration of an ultrasound system according to Embodiment 2 of the invention.

As illustrated in FIG. 8, an ultrasound system 1A according to Embodiment 2 of the invention comprises an ultrasound probe 2A and an image display device 3A.

The ultrasound probe 2A according to Embodiment 2 is different from the ultrasound probe 2 according to Embodiment 1 illustrated in FIG. 1 in that the image processing unit 17 is removed and a probe control unit 22A is provided instead of the probe control unit 22. The image display device 3A according to Embodiment 2 is different from the image display device 3 according to Embodiment 1 illustrated in FIG. 1 in that the image processing unit 17 is added and a main body control unit 38A is provided instead of the main body control unit 38.

In the ultrasound probe 2A, the compression unit 18 is directly connected to the signal processing unit 16, and the signal processing unit 16 forms an image information data generation unit 20A. Further, the probe control unit 22A is connected to the ultrasound transmission and reception control unit 15, the signal processing unit 16, the compression unit 18, the communication control unit 21, and the compression ratio setting unit 23. Furthermore, the transmitting unit 12, the receiving unit 13, the ultrasound transmission and reception control unit 15, the signal processing unit 16, the compression unit 18, the communication control unit 21, the probe control unit 22A, and the compression ratio setting unit 23 form a probe-side processor 25A.

In the image display device 3A, the image processing unit 17 is connected to the decompression unit 33 and the storage control unit 34 is connected to the image processing unit 17. Further, the main body control unit 38A is connected to the image processing unit 17, the decompression unit 33, the storage control unit 34, the display control unit 35, the communication control unit 37, the inspection mode setting unit 39, the operation unit 40, and the storage unit 41. Furthermore, the image processing unit 17, the decompression unit 33, the storage control unit 34, the display control unit 35, the communication control unit 37, the main body control unit 38A, and the inspection mode setting unit 39 form a display-device-side processor 43A.

First, the inspection mode setting unit 39 of the display-device-side processor 43A sets an inspection mode used for diagnosis of the B-mode and the M-mode. Information indicating the inspection mode set by the inspection mode setting unit 39 is wirelessly transmitted to the probe-side wireless communication unit 19 of the ultrasound probe 2A through the display-device-side wireless communication unit 32 of the image display device 3A and is then transmitted to the probe control unit 22A of the probe-side processor 25A. In addition, the information indicating the inspection mode used for diagnosis is transmitted from the probe control unit 22A to the ultrasound transmission and reception control unit 15, the compression unit 18, and the compression ratio setting unit 23.

The ultrasound transmission and reception control unit 15 of the probe-side processor 25A controls the transmitting unit 12 and the receiving unit 13 of the transmitting and receiving unit 14 on the basis of the information indicating the inspection mode transmitted from the probe control unit 22A such that the transducer array 11 transmits and receives ultrasonic waves.

In this case, under the control of the ultrasound transmission and reception control unit 15, the plurality of transducers of the transducer array 11 transmit ultrasound beams according to a driving signal from the transmitting unit 12 of the transmitting and receiving unit 14 and each transducer that has received ultrasound echoes from the subject outputs an analog reception signal to the receiving unit 13. The amplification unit 26 amplifies the reception signal and the AD conversion unit 27 performs AD conversion on the reception signal to acquire reception data. Then, the beam former 28 performs the reception focusing process to generate a sound ray signal.

The image information data generation unit 20A of the probe-side processor 2B performs a predetermined process on the sound ray signal generated by the beam former 28 of the receiving unit 13. Then, the image information data generation unit 20A generates, as the image information data, a signal subjected to an envelope detection process and a signal in which signal intensity in the depth direction along the set scanning line is plotted on the time axis.

In this case, the B-mode processing unit 29 of the signal processing unit 16 illustrated in FIG. 3 corrects the attenuation of the sound ray signal generated by the beam former 28 of the receiving unit 13 caused by a propagation distance according to the depth of the position where the ultrasonic waves are reflected and performs the envelope detection process on the sound ray signal to generate, as the image information data, a signal that is tomographic image information related to the tissues in the subject.

The M-mode processing unit 30 of the signal processing unit 16 plots signal intensity in the depth direction along the set scanning line on the time axis and generates a signal indicating a time-series change in the tissues of the subject as the image information data.

The compression ratio setting unit 23 of the probe-side processor 25A sets a compression ratio for compressing the signal generated by the image information data generation unit 20A on the basis of the information indicating the inspection mode transmitted from the probe control unit 22A. For example, the compression ratio setting unit 23 sets the compression ratio according to whether the inspection mode transmitted from the probe control unit 22A is the B-mode which is the frame unit mode or the M-mode which is the scroll mode. Therefore, for example, in a case in which the inspection mode used for diagnosis is the M-mode which is the scroll mode, the compression ratio is set to a small value. As a result, intensity unevenness at each separation time Wt in the signal generated by the M-mode processing unit 30 is suppressed.

The compression unit 18 of the probe-side processor 25A compresses the signal generated by the signal processing unit 16 as two-dimensional data, using the compression ratio set by the compression ratio setting unit 23, on the basis of the information indicating the inspection mode transmitted from the probe control unit 22A. In this case, the compression unit 18 compresses the signal generated by the signal processing unit 16 using, for example, a compression format such as JPEG. Here, in a case in which the information indicating the inspection mode transmitted from the probe control unit 22A is information indicating the B-mode, the compression unit 18 compresses the signal generated by the B-mode processing unit 29 of the signal processing unit 16 in units of frames. Further, in a case in which the information indicating the inspection mode transmitted from the probe control unit 22A is information indicating the M-mode, the compression unit 18 divides and compresses the signal generated by the M-mode processing unit 30 of the signal processing unit 16 at an interval of the predetermined separation time Wt.

The probe-side wireless communication unit 19 of the ultrasound probe 2A modulates a carrier on the basis of the signal compressed by the compression unit 18 to generate a transmission signal indicating the signal subjected to the envelope detection process and a transmission signal indicating the signal in which signal intensity is plotted on the time axis, and wirelessly transmits the generated transmission signals to the display-device-side wireless communication unit 32 of the image display device 3A.

The display-device-side wireless communication unit 32 of the image display device 3A demodulates the transmission signal indicating the signal subjected to the envelope detection process and the transmission signal indicating the signal in which signal intensity is plotted on the time axis, which have been wirelessly transmitted from the probe-side wireless communication unit 19 of the ultrasound probe 2A, and outputs the signal subjected to the envelope detection process and the signal in which signal intensity in the depth direction along the set scanning line is plotted on the time axis to the decompression unit 33 of the display-device-side processor 43A.

The decompression unit 33 decodes the signals output by the display-device-side wireless communication unit 32 of the image display device 3A on the basis of the compression format used.

The image processing unit 17 of the display-device-side processor 43A raster-converts the signals decoded by the decompression unit 33 into image signals following a general television signal scanning method and performs various kinds of necessary image processing, such as brightness correction, gradation correction, sharpness correction, and color correction, to generate, as the image information data, a B-mode image signal corresponding to a tomographic image of the tissues of the subject and an M-mode image signal corresponding to an image indicating a time-series change in the tissues of the subject. In this case, the image processing unit 17 generates the B-mode image signal on the basis of the signal subjected to the envelope detection process and generates the M-mode image signal on the basis of the signal in which signal intensity in the depth direction along the set scanning line is plotted on the time axis.

The B-mode image signal and the M-mode image signal generated by the image processing unit 17 are stored in the image memory 42 of the image display device 3A under the control of the storage control unit 34 of the display-device-side processor 43A. The B-mode image and the M-mode image based on the B-mode image signal and the M-mode image signal stored in the image memory 42 are displayed on the display unit 36 through the display control unit 35. Here, the compression ratio setting unit 23 of the probe-side processor 25A sets the compression ratio corresponding to the M-mode. In the signal which has been generated by the M-mode processing unit 30 of the signal processing unit 16 and then divided and compressed by the compression unit 18, intensity unevenness at each predetermined separation time Wt is suppressed. Therefore, unevenness at each separation time Wt is also suppressed in the M-mode image displayed on the display unit 36.

As described above, according to the ultrasound system 1A according to Embodiment 2, the image processing unit 17 is not provided in the ultrasound probe 2A, but is provided in the image display device 3A. In this configuration, similarly to Embodiment 1, in a case in which the M-mode image is displayed on the display unit 36, unevenness at each predetermined separation time Wt is suppressed. Therefore, even in a case in which the ultrasound probe 2A and the image display device 3A are wirelessly connected to each other, it is possible to display a high-quality ultrasound image regardless of the inspection mode.

It is preferable that the image information data wirelessly transmitted from the ultrasound probe 2 to the image display device 3 in Embodiment 1 and the image information data wirelessly transmitted from the ultrasound probe 2A to the image display device 3A in Embodiment 2 are signals after detection. However, the image information data is not limited to the signal after detection.

In the image display devices 3 and 3A according to the above-described Embodiments 1 and 2, a touch sensor may be combined with the display unit 36 and may be used as the operation unit 40. In a case in which the image display devices 3 and 3A are configured in this way, they are also very effective for outdoor diagnosis during, for example, emergency treatment.

EXPLANATION OF REFERENCES 1, 1A: ultrasound system
2, 2A: ultrasound probe
3, 3A: image display device
11: transducer array
12: transmitting unit
13: receiving unit
14: transmitting and receiving unit
15: ultrasound transmission and reception control unit
16: signal processing unit
17: image processing unit
18: compression unit
19: probe-side wireless communication unit
20, 20A: image information data generation unit
21, 37: communication control unit
22, 22A: probe control unit
23: compression ratio setting unit
24: battery
25, 25A: probe-side processor
26: amplification unit
27: AD conversion unit
28: beam former
29: B-mode processing unit
30: M-mode processing unit
32: display-device-side wireless communication unit
33: decompression unit
34: storage control unit
35: display control unit
36: display unit
38, 38A: main body control unit
39: inspection mode setting unit
40: operation unit
41: storage unit
42: Image memory
43, 43A: display-device-side processor
M, M1, M2: M-mode image signal
RB: black region
RS: scroll display region
SL: scanning line
TD1, TD2, TD3, T1 to T6: time
U1: first unit of storage
U2: second unit of storage
UB: B-mode image
UM, UM1 to UM6: M-mode image
Ws: display length
Wt: separation time.

What is claimed is:

1. An ultrasound system comprising:
an ultrasound probe and an image display device that are wirelessly connected to each other,
wherein the ultrasound probe includes:
a transducer array;
a processor configured to:
generate a sound ray signal by directing the transducer array to transmit and receive ultrasonic waves,
generate image information data on the basis of the sound ray signal,
compress the image information data, and
set a compression ratio of the image information data; and
a wireless communication unit that wirelessly transmits the image information data compressed by the processor in the ultrasound probe to the image display device,
wherein the image display device includes:
a processor configured to:
decode the image information data wirelessly transmitted from the ultrasound probe, and
set an inspection mode to be performed among a plurality of predetermined inspection modes;
a display unit that displays an ultrasound image on the basis of the image information data decoded by the processor in the image display device; and
a wireless communication unit that wirelessly transmits a type of the inspection mode set by the processor in the image display device to the ultrasound probe, and
wherein the processor in the ultrasound probe is further configured to:
in a case in which the type of the inspection mode set by the processor in the image display device is a frame unit mode for displaying a first ultrasound image indicating a tomographic image of tissues of a subject as the ultrasound image in units of frames, set a predetermined first compression ratio, and
compress the image information data corresponding to the first ultrasound image at the first compression ratio, in a case in which the type of the inspection mode set by the processor in the image display device is a scroll mode for displaying a second ultrasound image indicating a time-series change in the tissues of the subject and extending toward one direction over time, as the ultrasound image, generate a plurality of divided image signals having a predetermined length in the one direction as the image information data by dividing the second ultrasound image at an interval of a predetermined time, set a second compression ratio for the plurality of the divided signals which is lower than the first compression ratio, and compress each of the plurality of divided image signals at the second compression ratio.

2. The ultrasound system according to claim 1, wherein the frame unit mode includes at least one of a brightness mode, a color Doppler mode, or a power Doppler mode, and the scroll mode includes at least one of a motion mode, a pulse Doppler mode, or a continuous wave Doppler mode.

3. The ultrasound system according to claim 1, wherein the image display device further includes an image memory that stores the image information data decoded by the processor in the image display device, and the processor in the image display device is further configured to control storage of the image information data in the image memory.

4. The ultrasound system according to claim 2, wherein the image display device further includes an image memory that stores the image information data decoded by the processor in the image display device, and the processor in the image display device is further configured to control storage of the image information data in the image memory.

5. The ultrasound system according to claim 3, wherein, in a case in which the inspection mode set by the processor in the image display device is the scroll mode, the display unit has a scroll display region having a predetermined display length for displaying the ultrasound image generated according to the scroll mode, and the processor in the image display device is further configured to store the image information data in the image memory, using a time width corresponding to the display length as a unit.

6. The ultrasound system according to claim 4, wherein, in a case in which the inspection mode set by the processor in the image display device is the scroll mode, the display unit has a scroll display region having a predetermined display length for displaying the ultrasound image generated according to the scroll mode, and the processor in the image display device is further configured to store the image information data in the image memory, using a time width corresponding to the display length as a unit.

7. The ultrasound system according to claim 1, wherein the image information data is a signal obtained by performing attenuation correction according to a depth of a reflection position of the ultrasonic waves and an envelope detection process on the sound ray signal generated by the processor in the ultrasound probe.

8. The ultrasound system according to claim 2, wherein the image information data is a signal obtained by performing attenuation correction according to a depth of a reflection position of the ultrasonic waves and an envelope detection process on the sound ray signal generated by the processor in the ultrasound probe.

9. The ultrasound system according to claim 3, wherein the image information data is a signal obtained by performing attenuation correction according to a depth of a reflection position of the ultrasonic waves and an envelope detection process on the sound ray signal generated by the processor in the ultrasound probe.

10. The ultrasound system according to claim 1, wherein the image information data is an ultrasound image signal obtained by performing attenuation correction according to a depth of a reflection position of the ultrasonic waves and an envelope detection process on the sound ray signal generated by the processor in the ultrasound probe and converting the sound ray signal according to a predetermined image display method.

11. The ultrasound system according to claim 2, wherein the image information data is an ultrasound image signal obtained by performing attenuation correction according to a depth of a reflection position of the ultrasonic waves and an envelope detection process on the sound ray signal generated by the processor in the ultrasound probe and converting the sound ray signal according to a predetermined image display method.

12. The ultrasound system according to claim 3, wherein the image information data is an ultrasound image signal obtained by performing attenuation correction according to a depth of a reflection position of the ultrasonic waves and an envelope detection process on the sound ray signal generated by the processor in the ultrasound probe and converting the sound ray signal according to a predetermined image display method.

13. The ultrasound system according to claim 1, wherein the processor in the ultrasound probe is further configured to direct the transducer array to transmit the ultrasonic waves, and generate the sound ray signal on the basis of a reception signal acquired by the transducer array.

* * * * *